United States Patent [19]

White, Jr.

[11] 4,001,222

[45] Jan. 4, 1977

[54] 3-(AMINOACYL)-1-{[5-(SUBSTITUTED PHENYL)FURFURYLIDENE]AMINO}HYDANTOINS AND PROCESS FOR THE PREPARATION THEREOF

[75] Inventor: Ralph L. White, Jr., Norwich, N.Y.

[73] Assignee: Morton-Norwich Products, Inc., Norwich, N.Y.

[22] Filed: Oct. 14, 1975

[21] Appl. No.: 622,262

[52] U.S. Cl. .......................... 260/240 G; 260/309.5
[51] Int. Cl.$^2$ ........................................ C07D 405/06
[58] Field of Search ..................... 260/240 G, 309.5

[56] References Cited

UNITED STATES PATENTS

| | | | |
|---|---|---|---|
| 3,415,821 | 12/1968 | Davis et al. | 260/240 G |
| 3,843,636 | 10/1974 | White, Jr. | 260/240 G |

*Primary Examiner*—Allen B. Curtis
*Attorney, Agent, or Firm*—Anthony J. Franze

[57] ABSTRACT

A series of 3-(aminoacyl)-1-{[5-(substituted phenyl)-furfurylidene]amino}hydantoins are useful as muscle relaxants. A process for their preparation is also described.

11 Claims, No Drawings

3-(AMINOACYL)-1-[5-(SUBSTITUTED PHENYL)FURFURYLIDENE]AMINO HYDANTOINS AND PROCESS FOR THEIR PREPARATION THEREOF

This invention is concerned with chemical compounds. More particularly it is concerned with a series of 3-(aminoacyl)-1-{[5-(substituted phenyl)-furfurylidene]amino}hydantoins of the formula:

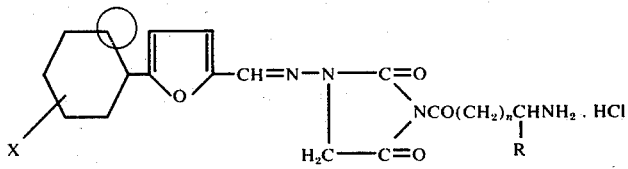

wherein X is 4-nitro, 3,4-dichloro, 4-fluoro, 4-chloro, 4cyano, or 4-methoxy; n is 0–4; and R is hydrogen, methyl or benzyl.

The members of this series possess pharmacologic activity. They are particularly useful as muscle relaxants. Thus, when administered intravenously to rats in a physiologically acceptable menstruum such as tetrahydrofurfuryl alcohol or dimethylsulfoxide at a dose of from 1–25 mg/kg, muscle relaxant effects are elicited.

The method which is currently preferred for the preparation of members of this series is illustrated by the following schema wherein X, n, and R have the significance ascribed above and "t-BOC" is tertiary butoxycarbonyl:

In order that this invention may be readily available to and understood by those skilled in the art the following examples of the preparation of members of the series are appended. In these examples the tertiary butoxycarbonyl derivative of the amino acid is prepared in accordance with the procedure described in J. Chem. Soc. 1964, 6130.

EXAMPLE I 3-(3-Aminopropionyl)-1-{[5-(4-nitrophenyl)furfurylidene]amino}hydantoin Hydrochloride t-Butoxycarbonyl-β-alanine (14 g, 0.075 mole) in dimethylformamide (350 ml) was cooled to 0° and triethylamine (21 ml, 0.15 mole) was added rapidly. The solution was maintained at −5° to −10° while isobutylchloroformate (10.5 ml, 0.075 mole) was added. The stirred solution was kept at −5° for 10 minutes and then solid 1-{[5-(4-nitrophenyl)furfurylidene]amino}hydantoin (21 g, 0.068 mole) was added over 5 minutes. The temperature was maintained at −5° to 0° for 30 minutes and then was stirred 1 hour without cooling. The dimethylformamide solution was poured into a stirred solution of ice water (3.0 l) containing conc. hydrochloric acid (50 ml). The resulting yellow solid was collected and air dried. Recrystallization from acetonitrile (2.5 l) yielded 17 g (51%) of intermediate product, m.p. 213°–214°.

The 3-(t-butoxycarbonyl-aminopropionyl)-1-{[5-(4-nitrophenyl)furfurylidene]amino}hydantoin (17g,

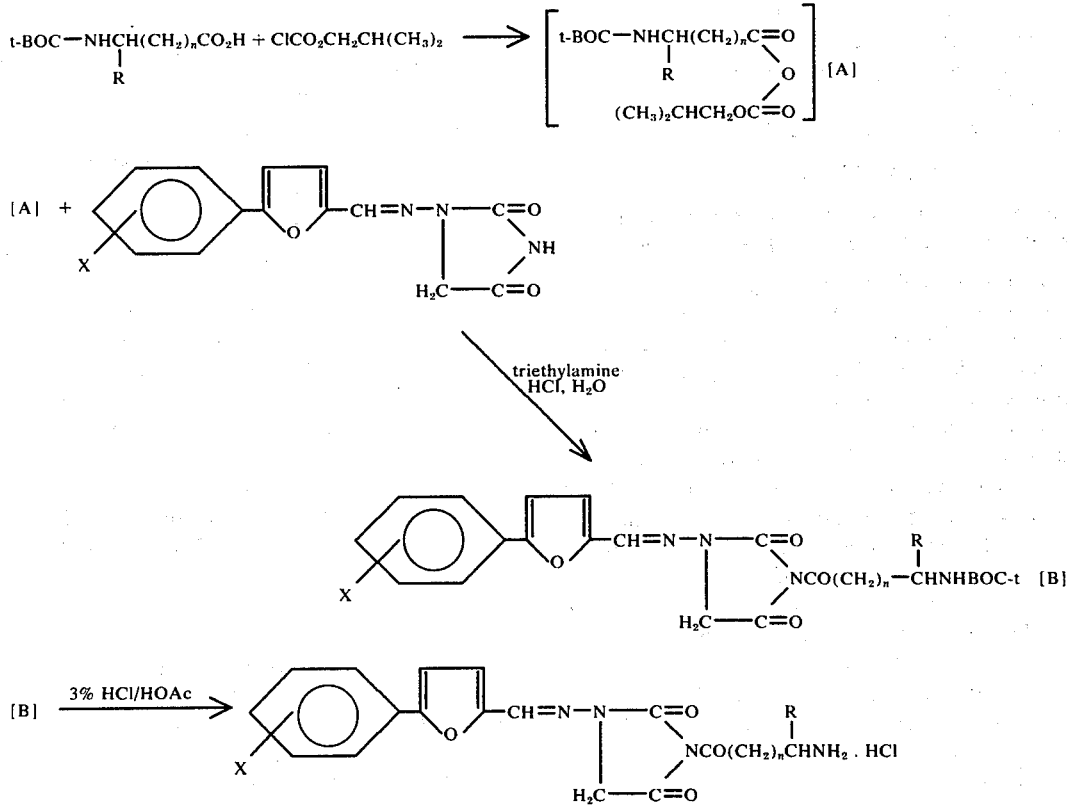

0.035 mole) was added to 3% hydrochloric acid/acetic acid (400 ml) at 15° and was stirred for 5 hours. The mixture was filtered and the collected solid was washed with nitromethane (200 ml) and ether (100 ml). The solid was dried in a 60° oven overnight yielding 14 g (94%, 48% overall) m.p. 211°–212°.

Anal. Calcd. for $C_{17}H_{15}N_5O_6 \cdot HCl$: C, 48.41; H, 3.82; N, 16.61. Found: C, 48.44; H, 3.95; N, 16.92.

EXAMPLE II 3-(3-Aminopropionyl)-1-{[5-(3,4-dichlorophenyl)-furfurylidene]amino hydantion}Hydrochloride t-Butoxycarbonyl-β-alanine (14.9 g, 0.08 mole) in dimethylformamide (375 ml) was cooled to 0°, and triethylamine (22.4 ml, 0.16 mole) was rapidly added. The solution was kept at −5° to −10° while isobutylchloroformate was added dropwise (11.2 ml, 0.08 mole). The solution was stirred for 10 minutes before the addition of 1-{[5-(3,4-dichlorophenyl)furfurylidene]amino}hydantoin (22.4 g, 0.073 mole). The temperature was maintained below 0° for 30 minutes and then stirred 1 hour without cooling. The solution was poured into a solution of 3200 ml of ice water and 50 ml conc. HCl.

The yellow solid was air dried and recrystallized in acetonitrile (350 ml) to yield 18.4 g.

The 3-(t-butoxycarbonyl-aminopropionyl)-1-{[5-(3-4-dichlorophenyl) furfurylidene]amino}hydantoin (18.4 g, 0.036 mole) was added to 3% HCl/acetic acid (400 ml) and stirred for 4 hours. The solid was filtered, washed with nitromethane and ether to yield 11.4 g (45% overall yield), m.p. 199°–202°.

Anal. Calcd. for $C_{17}H_{14}Cl_2N_4O_4 \cdot HCl$: C, 45.81; H, 3.39; N, 12.57.

Found: C, 45.81; H, 3.33; N, 12.45.

EXAMPLE III 3-(3-Aminopropionyl)-1-{[5-(4-fluorophenyl)furfurylidene]amino}hydantoin Hydrochloride t-Butoxycarbonyl-β-alanine (13.0 g, 0.07 mole) in dimethylformamide (325 ml) was cooled to 0°, and triethylamine (19.6 ml, 0.14 mole) was rapidly added. The solution was kept at −5° to −10° C while isobutylchloroformate was added dropwise (9.8 ml, 0.07 mole). The solution was stirred for 10 minutes before the addition of 1-{[5-(4-fluorophenyl)furfurylidene]amino}hydantoin (18.1 g, 0.063 mole). The temperature was maintained below 0° for 30 minutes, and then stirred 1 hour without cooling. The solution was poured into a solution of 2800 ml of ice water and 45 ml of concentrated hydrochloric acid. The resulting solid was collected, air-dried and recrystallized in nitromethane (400ml) to yield 10.4 g.

The 3-(t-butoxycarbonyl-aminopropionyl)-1-{[5-(4-fluorophenyl) furfurylidene]amino}hydantoin (10.4 g, 0.023 mole) was added to 3% HCl/acetic acid (125 ml) and stirred for 4 hours. The yellow solid was filtered, washed with nitromethane and ether to yield 7 g, 28%, m.p. 195°–197° C.

Anal. Calcd. for $C_{17}H_{14}FN_4O_4 \cdot HCl$: C, 51.72; H, 4.08; N, 14.19.

Found: C, 51.96; H, 4.18; N, 13.94.

EXAMPLE IV 3-(3-aminopropionyl)-1-{[5-(4-chlorophenyl)furfurylidene]amino}hydantoin Hydrochloride t-Butoxycarbonyl-β-alanine (18.9 g, 0.10 mole) in dimethylformamide (452 ml) was cooled to 0°, and triethylamine (14.7 g, 0.147 mole) was rapidly added. The solution was maintained at −5° to −10° while isobutylchloroformate (13.6 ml, 0.10 mole) was added. The stirred solution was kept at −5° for 10 minutes and then solid 1-{[5-(4-chlorophenyl)furfurylidene]amino}hydantoin (27.6 g, 0.090 mole) was added over 5 minutes. The temperature was maintained at −5° to 0° for 30 minutes and then was stirred 1 hour without cooling. The solution was stirred into 3,600 ml of ice water containing 55 ml of concentrated hydrochloric acid. The solid was collected and air-dried, which yielded 47 g (122%) of intermediate product.

The 3-(t-butoxycarbonyl-aminopropionyl)-1-{[5-(4-chlorophenyl) furfurylidene]amino}hydantoin (47 g, 0.11 mole) was added to 3% hydrochloric acid/acetic acid (500 ml) and was stirred for 2 hours. The mixture was filtered and the collected solid was washed with nitromethane and ether which yielded 30.5 g (82% overall), m.p. 242°–245°.

Anal. Calcd. for $C_{17}H_{15}ClN_4O_4 \cdot HCl$: C, 49.77; H, 3.69; N, 13.66.

Found: C, 49.90; H, 3.87; N, 13.48.

EXAMPLE V 3-(2-Aminopropionyl)-1-{[5-(3,4-dichlorophenyl)furfurylidene]amino} hydantoin Hydrochloride t-Butoxycarbonyl-α-alanine (18.9 g, 0.10 mole) in dimethylformamide (425 ml) was cooled to 0°, and triethylamine (20.2 ml, 0.147 mole) was rapidly added. The solution was maintained at −5° to −10° while isobutylchloroformate (13.6 ml, 0.10 mole) was added. The stirred solution was kept at −5° for 10 minutes and then solid 1-{[5-(3,4-dichlorophenyl)furfurylidene]amino}hydantoin (30.4 g, 0.09 mole) was added over 5 minutes. The temperature was maintained at −5° to 0° for 30 minutes and then was stirred 1 hour without cooling. The solution was stirred into 3,600 ml of ice water containing 55 ml concentrated hydrochloric acid. The solid was collected and air-dried. Recrystallization from acetonitrile yielded a first crop of unreacted 1-{[5-(3,4-dichlorophenyl)furfurylidene]amino}hydantoin. The second two crops were combined for a yield of 15 g (36% of intermediate product).

The 3-[2-(t-butoxycarbonyl-amino)propionyl]-1-{[5-(3,4-dichlorophenyl)furfurylidene]amino}hydantoin (15.1 g, 0.033 mole) was added to 3% hydrochloric acid/acetic (185 ml) and was stirred for 2 hours. The mixture was filtered and the collected solid was washed with nitromethane and ether which yielded 10.4 g (70%, 25% overall), m.p. 192°–196°.

Anal. Calcd. for $C_{17}H_{14}Cl_2N_4O_4 \cdot HCl$: C, 45.81; H, 3.39; N, 12.57.

Found: C, 45.98; H, 3.41; N, 12.65.

EXAMPLE VI

3-(3-Aminopropionyl)-1-{[5-(4-cyanophenyl)furfurylidene]amino}hydantoin Hydrochloride t-Butoxycarbonyl -β-alanine (16.1 g, 0.080 mole) in dimethylformamide (200 ml) was cooled to 0°, and triethylamine (23.8 ml, 0.17 mole) was rapidly added. The solution was kept at −5° to 0° while isobutylchloroformate (11.9 ml, 0.085 mole) was added dropwise. The solution was stirred 10 minutes and then 1-{[5-(4-cyanophenyl)furfurylidene]amino}hydantoin (recrystallized and predried at 100° overnight; 23.5 g, 0.080 mole) was rapidly added. The mixture was maintained at −5° to 0° for 0.5 hr and was then stirred 1 hour without cooling. The mixture was poured into a solution of ice water (1,400 ml) and concentrated hydrochloric acid (25 ml). The resulting solid was collected and air-dried. The product was dissolved in acetonitrile, filtered, and concentrated to a solid.

The crude t-butoxycarbonyl intermediate was placed in a 500 ml flask equipped with stirrer and drying tube and 3% HCl/acetic acid (200 ml) was introduced. The mixture was stirred 6 hours then filtered and the collected solid was rinsed with diethyl ether (three 100 ml portions). The dried product was placed in nitromethane (500 ml). The mixture was brought to reflux then filtered hot to yield 20 g (62%), m.p. 193°–194° (dec.).

Anal. Calcd. for $C_{18}H_{15}N_5O_4 \cdot HCl$: C, 53.80; H, 4.01; N, 17.43.

Found: C, 53.55; H, 4.05; N, 17.30.

EXAMPLE VII

3-(6-Aminohexanoyl)-1-{[5-(3,4-dichlorophenyl)furfurylidene]amino}hydantoin Hydrochloride 6-(t-Butoxycarbonyl-amino)hexanoic acid (16.2 g, 0.07 mole) in dimethylformamide (325 ml) was cooled to 0°, and triethylamine (19.6 ml, 0.14 mole) was rapidly added. The solution was maintained at −5° to −10° while isobutylchloroformate (9.8 ml, 0.07 mole) was added. The stirred solution was kept at −5° for 10 minutes and then solid 1-{[5-(3,4-dichlorophenyl)furfurylidene]amino}-hydantoin (23.7 g, 0.07 mole) was added over 5 minutes. The temperature was maintained at −5° to 0° for 30 minutes and then stirred for 30 minutes without cooling. The dimethylformamide solution was poured into a stirred solution of ice water (2,800 ml) containing concentrated hydrochloric acid (45 ml). The resulting yellow solid was collected by filtration and stirred in ether (200 ml), filtered and air-dried with a yield of 29 g (74%) of intermediate product.

The 3(t-butoxycarbonyl-aminohexanoyl)-1-{[5-(3,4-dichlorophenyl)furfurylidene]amino}hydantoin (29 g, 0.052 mole) was added to 3% hydrochloric acid/acetic acid (650 ml) and stirred for 2 hours. The mixture was filtered and the collected solid was washed with nitromethane and ether, then heated to boiling in nitromethane and filtered again, yielding 10 g (38%, 28% overall), m.p. 205°–207°.

Anal. Calcd. for $C_{20}H_{20}Cl_2N_4O_4 \cdot HCl$: C, 49.24; H, 4.34; N, 11.49.

Found: C, 49.24; H, 4.30; N, 11.51.

EXAMPLE VIII

3-(2-Amino-3-phenylpropionyl)-1-{[5-(3,4-dichlorophenyl)furfurylidene]amino}hydantoin Hydrochloride t-Butoxycarbonyl-phenylalanine (6.1 g, 0.023 mole) in 100 ml dimethylformamide was cooled to 0°, and triethylamine (6.4 ml, 0.046 mole) was rapidly added. The solution was maintained at below −10° while isobutylchloroformate (3.2 ml, 0.023 mole) was added dropwise. The stirred solution was kept at −10° for 10 minutes before solid 1-{[5-(3,4-dichlorophenyl)furfurylidene]amino}hydantoin (7.1 g, 0.021 mole) was added. The temperature was maintained at −10° for 30 minutes, and then allowed to warm up for 30 minutes. The solution was poured into a stirred solution of 900 ml ice water and 15 ml concentrated hydrochloric acid. The resulting yellow solid was collected and air-dried (yield: 12.5 g of intermediate product).

The 3-(t-butoxycarbonyl-amino-3-phenylpropionyl)-1-{[5-(3,4-dichlorophenyl)furfurylidene]amino}hydantoin (12.6 g, 0.022 mole) was added to 3% hydrochloric acid/acetic acid (200 ml) and stirred for 2 hours. The mixture was filtered and the collected solid was washed with nitromethane and ether. The solid was air-dried and yielded 5.6 g (52% overall) m.p. 152°–160°.

Anal. Calcd. for $C_{23}H_{18}Cl_2N_4O_4 \cdot HCl$: C, 52.94; H, 3.67; N, 10.74.

Found: C, 52.66; H, 3.85; N, 10.67.

EXAMPLE IX

3-(3-Aminopropionyl)-1-{[5-(4-methoxyphenyl)furfurylidene]amino}hydantoin Hydrochloride To a stirred solution of t-butoxycarbonyl-β-alanine (9.5 g, 0.05 mole) in dimethylformamide (200 ml), cooled to 0°, was added triethylamine (14 ml, 0.10 mole) rapidly. The stirred solution was kept below 0° as isobutyl chloroformate (7.0 ml, 0.05 mole) was added dropwise over a period of 5 minutes. The mixture was stirred for 10 minutes at 0° before 1{[5-(4-methoxyphenyl)furfurylidene]amino}hydantoin (15 g, 0.05 mole) was added. The solution was stirred for 1 hour at 0° and 1 hour at room temperature. The solution was poured into a mixture of ice and water (1,700 ml) and conc. HCl (27 ml). The precipitated solid was collected by filtration and allowed to air dry. Recrystallization from ethanol (1,200 ml) gave 15.2 g (65%), m.p. 258°–262°.

A mixture of the above t-butoxycarbonyl derivative (14.7 g, 0.031 mole) and 3% HCl/acetic acid (400 ml) was stirred for 5 hours at room temperature. The mixture was added to anhydrous ether and after standing overnight at room temperature, a yellow solid precipitated. The yellow solid was collected by filtration, and when the solid was exposed to the air it turned gummy. The gummy material was triturated first with nitromethane and then ether to give 8.1 g (40%) of product, m.p. 190° (dec.).

Anal. Calcd. for $C_{18}H_{18}N_4O_5 \cdot HCl$: C, 53.14; H, 4.71; N, 13.77.

Found: C, 53.41; H, 4.93; N, 13.71.

What is claimed is:

1. A compound of the formula:

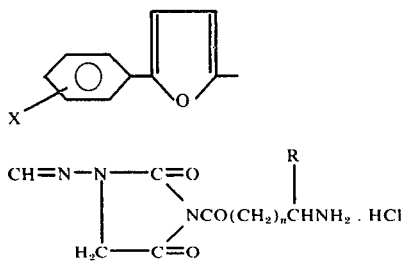

wherein X is 4-nitro, 3,4-dichloro, 4-fluoro, 4-chloro, 4-cyano, or 4-methoxy, $n$ is 0–4; and R is hydrogen, methyl or benzyl.

2. The compound 3-(3-aminopropionyl)-1{[5-(4-nitro)furfurylidene]amino} hydantoin hydrochloride.

3. The compound 3-(3-aminopropionyl)-1-{[5-(3,4-dichlorophenyl)furfurylidene]amino} hydantoin hydrochloride.

4. The compound 3-(3-aminopropionyl)-1-{[5-(4-fluorophenyl)furfurylidene]amino} hydantoin hydrochloride.

5. The compound 3-(3-aminopropionyl)-1-{[5-(4-chlorophenyl)furfurylidene]amino} hydantoin hydrochloride.

6. The compound 3-(2-aminopropionyl)-1-{[5-(3,4-dichlorophenyl)furfurylidene]amino} hydantoin hydrochloride.

7. The compound 3-(3-aminopropionyl)-1-{[5-(4-cyanophenyl)furfurylidene]amino} hydantoin hydrochloride.

8. The compound 3-(6-aminohexanoyl)-1-{[5-(3,4-dichlorophenyl)furfurylidene]amino} hydantoin hydrochloride.

9. The compound 3-(2-amino-3-phenylpropionyl)-1-{[5-(3,4-dichlorophenyl)furfurylidene]amino}hydantoin hydrochloride.

10. The compound 3-(3-aminopropionyl)-1-{[5-(4-methoxyphenyl)furfurylidene]amino} hydantoin hydrochloride.

11. The method of making a compound of the formula:

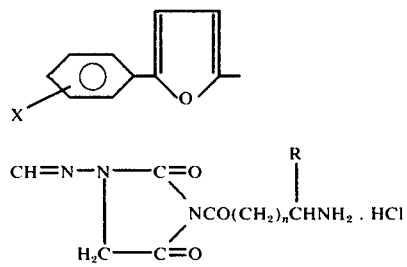

which comprises hydrolyzing a compound of the formula:

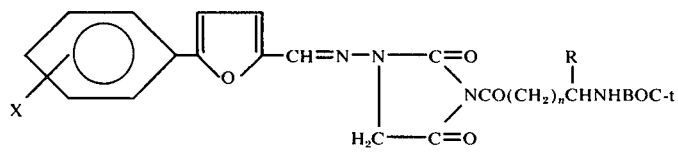

wherein X, $n$ and R have the significance aforestated and BOC-t is tertiary butoxycarbonyl with 3% hydrochloric acid in acetic acid.

* * * * *